(12) United States Patent
Sainani

(10) Patent No.: US 8,143,436 B2
(45) Date of Patent: Mar. 27, 2012

(54) PROCESS FOR PREPARING ALKYL ALKOXYBENZOATES IN ONE STEP

(75) Inventor: Jaiprakash Brijlal Sainani, Vadodara (IN)

(73) Assignee: Saudi Basic Industries Corporation, Riyadh (SA)

( * ) Notice: Subject to any disclaimer, the term of this patent is extended or adjusted under 35 U.S.C. 154(b) by 47 days.

(21) Appl. No.: 12/451,109

(22) PCT Filed: Apr. 23, 2008

(86) PCT No.: PCT/EP2008/003257
§ 371 (c)(1),
(2), (4) Date: Mar. 1, 2010

(87) PCT Pub. No.: WO2008/138457
PCT Pub. Date: Nov. 20, 2008

(65) Prior Publication Data
US 2010/0152476 A1    Jun. 17, 2010

(30) Foreign Application Priority Data
May 10, 2007   (IN) .......................... 1015/DEL/2007

(51) Int. Cl.
*C07C 69/00*   (2006.01)
(52) U.S. Cl. ...................................................... 560/64
(58) Field of Classification Search ........................ None
See application file for complete search history.

(56) References Cited

FOREIGN PATENT DOCUMENTS

| JP | 60 214753 A | 10/1985 |
|---|---|---|
| JP | 01 294654 A | 11/1989 |
| RO | 88669 | 3/1986 |

OTHER PUBLICATIONS

Stan Lee et al; "Process Development Fine Chemicals from Grams to Kilogrems, 10 Reagents for Large Scale Operation"; p. 76; Oxford U. Press; Oxford, GB ; Jan. 1, 1995.
Japanese Patent No. 60214753 (A); Publication Date: Oct. 28, 1985; Machine Translation; 4 Pages.
International Search Report; International Application No. PCT/EP2008/003257; International Filing Date Apr. 23, 2008; Date of Mailing Jul. 10, 2008; 10 pages.
Written Opinion of the International Searching Authority; PCT/EP2008/003257; International Filing Date Apr. 23, 2008; Date of Mailing Jul. 10, 2008; 6 pages.

*Primary Examiner* — Sudhakar Katakam
(74) *Attorney, Agent, or Firm* — Cantor Colburn LLP

(57) ABSTRACT

Process for preparing a compound of the formula

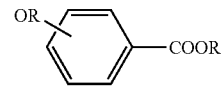

by contacting, in an organic solvent in the presence of an aqueous solution of a base, hydroxy benzoic acid with a compound of the formula $R_nX$, wherein R is an alkyl group having 1 to 6 C-atoms and X is an acid rest group having a valence n, wherein the organic solvent is an alkyl substituted aromatic hydrocarbon and the reaction is carried out at a pH of 8-10.

9 Claims, No Drawings

PROCESS FOR PREPARING ALKYL ALKOXYBENZOATES IN ONE STEP

The present invention relates to a process for preparing a compound of the formula:

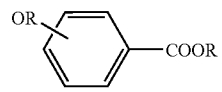

by contacting hydroxy benzoic acid with a compound of the formula $R_nX$, wherein R is an alkyl group having 1 to 6 carbon atoms and X is an acid rest group having a valency n.

The acid esters are useful as selective inhibitor in stereospecific polymerization. They are also used as starting materials in synthesis of various medicinal or drug compounds.

Processes for the preparation of said esters are known in the art. For example, in RO 88669 A, Ar(OR)n is alkylated with RX (X=Br, I, sulfate) at 20-30° C. in a polar aprotic solvent like dimethylsulfoxide, dimethylformamide or dimethylacetamide in the presence of 10-15% NaOH or KOH.

JP 60214753A discloses a one step process for preparing the esters from hydroxyl benzoic acid with several inert solvents, but the yields reported are poor and all below 60%.

Other processes start from potassium salts of aromatic hydroxy carboxylic acids using a phase transfer catalyst. Preparation of the potassium salts requires evaporation of water or mechanical grinding, which is not viable on industrial scale.

The known methods have several disadvantages like either use of a large excess of polar aprotic solvents, or use of ammonium salts as phase transfer catalyst that are difficult to break or neutralize, and which hence may pollute waste water. Other methods employ dry reaction at very high temperature, which is also industrially not feasible.

The main object of the invention is to provide a process for preparing alkyl benzoic acid alkyl ester in one step with a high yield using an organic solvent that can be easily recovered.

This aim is achieved according to the invention with a process wherein in an organic solvent in the presence of an aqueous solution of a base hydroxy benzoic acid is contacted with a compound of the formula $R_nX$, wherein R is an alkyl group having 1 to 6 C-atoms and X is an acid rest group having a valence n, and wherein the organic solvent is an alkyl substituted aromatic hydrocarbon and in that the reaction is carried out at a pH of 8-10.

Preferably a xylene, toluene or a mixture thereof is used as solvent. Xylene is understood to be o-xylene, m-xylene, p-xylene or mixtures thereof.

The process according to the invention allows preparing alkyl alkoxy benzoates in one step, starting from one single raw material, viz. aromatic hydroxyl carboxylic acid, with high yield of over 95% and without having to recover any intermediate or added compound.

The process comprises the production of a compound having formula (1)

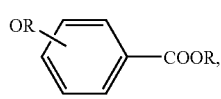

wherein R is an alkyl radical having 1 to 6, preferably 1 to 2 carbon atoms by reacting a compound of the formula (2)

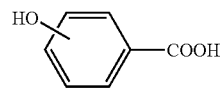

with a compound of the formula $R_nX$, wherein R is an alkyl group having 1 to 6 carbon atoms and X is an acid rest group having a valency n. The OH-group can be in the m-, o- or p-position.

Preferably R is an alkyl group having 1 or 2 carbon atoms.

Preferred acid rest groups are sulfates. Preferably $R_nX$ is a dialkylsulfate of the formula $(RO)_2SO_2$, in which R has the above meaning.

The amount of alkyl groups present in the amount of compound $R_nX$ is at least equal to the number of alkyl groups to be introduced in the amount of compound (2) and preferably exceeds this last amount by at least 20% and at most 100%. Preferably the excess of alkyl groups is between 25 and 50%.

The contacting takes place in the presence of an alkyl substituted aromatic hydrocarbon solvent, toluene or xylene being preferred and in the presence of a base in an aqueous solution. The amount of the base is chosen such that the pH value is in the range from 8 to 10 and preferably the process is carried out at a temperature above 70° C., preferably in the range of 80-95° C.

The benzene ring can be (mono- or di-) substituted with halogen atoms, alkyl groups having 1 to 4 C-atoms and/or alkoxy groups having 1 to 4 C-atoms.

The process according to invention allows converting hydroxy benzoic acid to corresponding alkoxy benzoic acid alkyl esters in one step with an excellent yield and purity. The reaction can be performed by adding hydroxy benzoic acid to a mixture of the organic solvent and the compound having the formula $R_nX$. An aqueous base solution is added to the mixture and the pH of the reaction is set between 8 and 10. The concentration of the base in the aqueous solution can be 10-50% and is preferably 25-40% and more preferably 30-40%. Sodium and potassium hydroxide are preferred as the base.

After completion of the base addition, the mass is stirred further for 15 minutes. Then the aqueous phase and the organic solvent phase are separated. The organic solvent layer is washed with water and distilled to give the pure product directly.

The invention is elucidated by the following illustrative experiments, without being restricted thereto.

Example I 15 g (0.108 mole) of 4-hydroxybenzoic acid and 54.4 g (0.353 mole) of diethylsulfate were introduced into a glass flask containing xylene (75 ml). The mixture was heated to 90° C. The pH of mass was checked by a calibrated pH electrode immersed in the mass. The pH was maintained between 8-10 by drop wise addition under stirring of a 35% aqueous NaOH solution [13.6 g (0.326 mole) NaOH flakes in 25 ml water] in 90 minutes. The mass is further stirred for 15 minutes after addition of NaOH. Then the mass was cooled to ambient temperature and 75 ml water was added. The upper organic phase containing the formed product was separated from the lower aqueous phase, washed with 2% NaOH aqueous solution (75 ml) and finally with water. Evaporation of solvent gave 20.5 g (97.6%) of p-ethoxy ethylbenzoate having purity 98.6% by HPLC.

Example 2

30 g (0.217 mole) of 4-hydroxybenzoic acid and 87.6 g (0.695 mole) of dimethylsulfate were introduced into a glass flask containing xylene (150 ml). The mixture was heated to 85° C. The pH of mass was checked by a calibrated pH electrode immersed in the mass. The pH was maintained between 8-10 by drop wise addition under stirring of a 76 gm (0.665 mole) 35% aqueous NaOH solution in 60 minutes. The mass is further stirred for 15 minutes after addition of NaOH. Then the mass was cooled to ambient temperature and 150 ml water was added. The upper organic phase containing the formed product was separated from the lower aqueous phase, washed with 2% NaOH aqueous solution (75 ml) and finally with water. Evaporation of solvent gave 35.3 g (98.05%) of p-methoxy methylbenzoate having purity 98.42% by HPLC.

Comparative Experiment A 15 g (0.108 mole) of 4-hydroxybenzoic acid and 54.4 g (0.353 mole) of diethylsulfate were introduced into a glass flask containing xylene (75 ml). The mixture was heated to 90° C. The pH of mass was checked by a calibrated pH electrode immersed in the mass. The pH was maintained between 6-7.5 by drop wise addition under stirring of a 35% aqueous NaOH solution [13.6 g (0.326 mole) NaOH flakes in 25 ml water] in 30 minutes. The mass is further stirred for 15 minutes after addition of NaOH. Then the mass was cooled to ambient temperature and 75 ml water was added. The upper organic phase containing the formed product was separated from the lower aqueous phase, washed with 2% NaOH aqueous solution (75 ml) and finally with water. Evaporation of solvent gave 15.3 g (72.8%) of p-ethoxy ethylbenzoate having purity 99.2% by HPLC.

It appears that the lower pH causes the yield to drop with respect to the working Examples, where the pH was kept between 8 and 10.

Comparative Experiment B 15 g (0.108 mole) of 4-hydroxybenzoic acid and 54.4 g (0.353 mole) of diethylsulfate were introduced into a glass flask containing xylene (75 ml). The mixture was heated to 90° C. The pH of mass was checked by a calibrated pH electrode immersed in the mass. The pH was maintained between 10.5 and 12 by drop wise addition of a 35% aqueous NaOH solution [13.6 g (0.326 mole) NaOH flakes in 25 ml water]. The mass is further stirred for 15 minutes and cooled to ambient temperature. The mass was diluted by addition of 75 ml water. The upper organic phase containing the formed product was separated from the lower aqueous phase, washed with 2% NaOH aqueous solution (75 ml) and finally with water. Evaporation of solvent gave 15.0 g (yield: 71.4%) of p-ethoxy ethylbenzoate having purity 96.57% by HPLC.

It appears that the higher pH causes the yield to drop with respect to the working Examples, where the pH was kept between 8 and 10.

The invention claimed is:

1. A process for preparing a compound of the formula

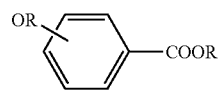

by contacting, in an organic solvent in the presence of an aqueous solution of a base, hydroxy benzoic acid with a compound of the formula $R_nX$, wherein R is an alkyl group having 1 to 6 C-atoms and X is an acid rest group having a valence n, characterized in that the organic solvent is an alkyl substituted aromatic hydrocarbon and in that the reaction is carried out at a pH of 8-10.

2. The process according to claim 1, wherein the organic solvent is at least one compound chosen from the group consisting of toluene and xylenes.

3. The process according to claim 1, wherein X is sulfate.

4. The process according to claim 1, wherein R is methyl or ethyl.

5. The process according to claim 1, wherein X is sulfate and R is methyl or ethyl.

6. The process according to claim 1, wherein the number of alkyl groups present in the amount of compound $R_nX$ is between 25 and 50% in excess to the number of hydroxyl and acid groups to be substituted.

7. The process according to claim 1, wherein the reaction is carried out at 80-95° C.

8. A process for preparing a compound of the formula

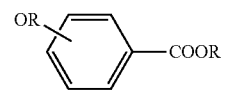

by contacting, in an organic solvent in the presence of an aqueous solution of a base, hydroxy benzoic acid with a compound of the formula $R_nX$,
  wherein R is methyl or ethyl and X is sulfate having a valence n,
  wherein the organic solvent is an alkyl substituted aromatic hydrocarbon and in that the reaction is carried out at a pH of 8-10;
  wherein the number of alkyl groups present in the amount of compound $R_nX$ is between 25 and 50% in excess to the number of hydroxyl and acid groups to be substituted; and
  wherein the reaction is carried out at 80-95° C.

9. A process for preparing a compound of the formula

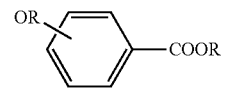

by contacting, in an organic solvent in the presence of an aqueous solution of a base, hydroxy benzoic acid with a compound of the formula $R_nX$,
  wherein R is an alkyl group having 1 to 6 C-atoms and X is an acid rest group having a valence n,
  wherein the organic solvent is an alkyl substituted aromatic hydrocarbon and in that the reaction is carried out at a pH of 8-10; and
  wherein the number of alkyl groups present in the amount of compound $R_nX$ is between 25 and 50% in excess to the number of hydroxyl and acid groups to be substituted.

* * * * *